US008771660B2

(12) United States Patent
Mitani et al.

(10) Patent No.: US 8,771,660 B2
(45) Date of Patent: Jul. 8, 2014

(54) METHOD OF SCREENING FOR A DAMP-DRY MALODOR INHIBITOR AND METHOD OF EVALUATING DAMP-DRY MALODOR INHIBITOR BY MICROBIAL PRODUCTION OF 4-METHYL-3-HEXENOIC ACID

(75) Inventors: Asako Mitani, Tokyo (JP); Hiromi Kubota, Mashiko-machi (JP); Yu Niwano, Wakayama (JP); Kohei Takeuchi, Funabashi (JP); Atsushi Tanaka, Hannan (JP); Noriko Yamaguchi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/823,851

(22) PCT Filed: Sep. 1, 2011

(86) PCT No.: PCT/JP2011/069950
§ 371 (c)(1),
(2), (4) Date: Apr. 19, 2013

(87) PCT Pub. No.: WO2012/039261
PCT Pub. Date: Mar. 29, 2012

(65) Prior Publication Data
US 2013/0210061 A1 Aug. 15, 2013

(30) Foreign Application Priority Data

Sep. 21, 2010 (JP) ................................ 2010-211459
Apr. 4, 2011 (JP) ................................ 2011-083031

(51) Int. Cl.
*A61L 9/00* (2006.01)

(52) U.S. Cl.
USPC ............................ 424/76.1; 424/76.4; 435/29

(58) Field of Classification Search
USPC ................... 424/76.1, 76.4; 435/29
See application file for complete search history.

(56) References Cited

FOREIGN PATENT DOCUMENTS

| JP | 56-124387 A | 9/1981 |
|---|---|---|
| JP | 2004-262900 A | 9/2004 |
| JP | 2004-263102 A | 9/2004 |
| JP | 2009-507477 A | 2/2009 |
| JP | 2009-244094 | 10/2009 |
| JP | 2009 244094 | * 10/2009 |
| JP | 2011-075385 A | 4/2011 |
| JP | 2011-177401 A | 9/2011 |
| JP | 2011-254807 A | 12/2011 |

OTHER PUBLICATIONS

Kubota H. et al. Moraxella Species are Primarily Responsible for Generating Malodor in Laundry. Applied and Evnironmental Microbiology 78(9)3317-3324, May 2012.*

International Search Report (ISR) for PCT/JP2011/069950; I.A. fd: Sep. 1, 2011, mailed Oct. 25, 2011 from the Japanese Patent Office, Tokyo, Japan.
International Preliminary Report on Patentability (IPRP), Chapter I of the Patent Cooperation Treaty, including the Written Opinion for PCT/JP2011/069950; I.A. fd: Sep. 1, 2011, issued Apr. 16, 2013, from the International Bureau of WIPO, Geneva, Switzerland.
Takeuchi, K. et al., "The analysis of the half-dried smell of the wearing apparel." ("Irui no Namakawakishu no Kaiseki"), Japan Society for Bioscience, Biotechnology, and Agrochemistry 2010 (Nendo Taikai Koen Yoshishu), Mar. 2010, abstract 3ACp23, p. 149, Tokyo, Japan.
Niwano, Y. et al., "Analysis cycle of microorganisms causing of laundry at daily wash cycle," ("Sentaku Cycle ni Okeru Irui no Namakawakishu Gen'in Kin Kaiseki") Fiber Preprints, Japan, vol. 66, No. 1 (Annual Meeting) abstract 2B03, p. 32, Jun. 2011.
Yoshizumi, A. et al., "Irui no Namakawakishu Gen'in Biseibutsu no Kaiseki," Japan Society for Bioscience, Biotechnology, and Agrochemistry 2011 (Nendo Taikai Koen Yoshishu), Mar. 2011, abstract 2C25p02, p. 102, Kyoto, Japan.
H. Hanihara et al., "The Detergent Curbing Malodor in Indoor Laundry Drying," Fragrance, No. 223, Sep. 2004, pp. 109-116.
Miyasato, H. et al., "Study on fragrance ingredient (III) of *Citrus junos* Tanaka," 53rd Symposium on the Chemistry of Terpenes, Essential Oils, and Aromatics, Nov. 7, 2009, No. 1A I-2, Symposium papers pp. 4-6, Nara, Japan.
Extended European search report including the supplementary European search report and the European search opinion, dated Apr. 15, 2014, for EP application No. 11826707.9, European Patent Office, Munich, Germany.
Munk, S. et al., "Microbial survival and odor in laundry," J. Surfactants and Detergents 4(4): 385-394 (Oct. 2001), AOCS Press, Champaign, IL.
Takeuchi, K. et al., "Identification of novel malodour compounds in laundry," Flavour and Fragrance Journal 27(1):89-94 (2012), published online Sep. 22, 2011, John Wiley & Sons, Ltd., New York, NY.
Takeuchi, K et al., "Review of odorants in human axillary odour and laundry malodour: The importance of branched C7 chain analogues in malodours perceived by humans," Flavour and Fragrance Journal 28(4):223-230 (2013), published online Nov. 28, 2012, John Wiley & Sons, Ltd., New York, NY.

* cited by examiner

*Primary Examiner* — Ralph Gitomer
(74) *Attorney, Agent, or Firm* — Sterne, Kessler, Goldstein & Fox P.L.L.C.

(57) ABSTRACT

A method of screening a damp-dry malodor inhibitor, containing the steps of: bringing microorganisms having a 4-methyl-3-hexenoic acid production capacity into contact with a test substance in the presence of a sebaceous dirt component, detecting the production of a damp-dry malodor-causing substance by the microorganisms, and thereby selecting a test substance having a damp-dry malodor inhibitory function; and a method of evaluating a damp-dry malodor inhibitor, containing the steps of: bringing microorganisms having a 4-methyl-3-hexenoic acid production capacity into contact with a test substance in the presence of a sebaceous dirt component, detecting the production of a damp-dry malodor-causing substance by the microorganisms, and thereby evaluating the damp-dry malodor inhibitory function of the test substance.

14 Claims, No Drawings

SEQUENCE LISTING

```
<160> NUMBER OF SEQ ID NOS: 3

<210> SEQ ID NO 1
<211> LENGTH: 1492
<212> TYPE: DNA
<213> ORGANISM: Moraxella sp. 4-1 strain

<400> SEQUENCE: 1
gagtttgatc ctggctcaga ttgaacgctg gcggcaggct taacacatgc aagtcgaacg      60
atgattatct agcttgctag atatgattag tggcggacgg gtgagtaaca tttaggaatc     120
tgcctagtag tggggatag ctcggggaaa ctcgaattaa taccgcatac gacctacggg     180
tgaaaggggg cgcaagctct tgctattaga tgagcctaaa tcagattagc tagttggtgg     240
ggtaaaggcc caccaaggcg acgatctgta actggtctga gaggatgatc agtcacaccg     300
gaactgagac acggtccgga ctcctacggg aggcagcagt ggggaatatt ggacaatggg     360
ggcaaccctg atccagccat gccgcgtgtg tgaagaaggc cttttggttg taaagcactt     420
taagcaggga ggagaggcta atggttaata cccattagat tagacgttac ctgcagaata     480
agcaccggct aactctgtgc cagcagccgc ggtaatacag agggtgcgag cgttaatcgg     540
aattactggg cgtaaagcga gtgtaggtgg ctcattaagt cacatgtgaa atccccgggc     600
ttaacctggg aactgcatgt gatactggtg gtgctagaat atgtgagagg gaagtagaat     660
tccaggtgta gcggtgaaat gcgtagagat ctggaggaat accgatggcg aaggcagctt     720
cctggcataa tattgacact gagattcgaa agcgtgggta gcaaacagga ttagataccc     780
tggtagtcca cgccgtaaac gatgtctact agccgttggg gtccttgaga ctttagtggc     840
gcagttaacg cgataagtag accgcctggg gagtacggcc gcaaggttaa aactcaaatg     900
aattgacggg ggcccgcaca agcggtggag catgtggttt aattcgatgc aacgcgaaga     960
accttacctg gtcttgacat agtgagaatc ctgcagagat gcgggagtgc cttcgggaat    1020
tcacatacag gtgctgcatg gctgtcgtca gctcgtgtcg tgagatgttg ggttaagtcc    1080
cgcaacgagc gcaacccttt tccttatttg ccagcgggtt aagccgggaa ctttaaggat    1140
actgccagtg acaaactgga ggaaggcggg gacgacgtca agtcatcatg gcccttacga    1200
ccagggctac acacgtgcta caatggtagg tacagagggt tgctacacag cgatgtgatg    1260
ctaatctcaa aaagcctatc gtagtccgga ttggagtctg caactcgact ccatgaagtc    1320
ggaatcgcta gtaatcgcag atcagaatgc tgcggtgaat acgttcccgg gccttgtaca    1380
caccgcccgt cacaccatgg gagtctattg caccagaagt aggtagccta acgmaagagg    1440
```

```
gcgcttacca cggtgtggtc gatgactggg gtgaagtcgt aacaaggtag cc         1492

<210> SEQ ID NO 2
<211> LENGTH: 1492
<212> TYPE: DNA
<213> ORGANISM: Moraxella sp. 4-4 strain

<400> SEQUENCE: 2
gagtttgatc ctggctcaga ttgaacgctg gcggcaggct taacacatgc aagtcgaacg   60
atgactctct agcttgctag agatgattag tggcggacgg gtgagtaaca tttaggaatc  120
tacctagtag tgggggatag ctcggggaaa ctcgaattaa taccgcatac gacctacggg  180
tgaaaggggg cgcaagctct tgctattaga tgagcctaaa tcagattagc tagttggtgg  240
ggtaaaggcc caccaaggcg acgatctgta actggtctga gaggatgatc agtcacaccg  300
gaactgagac acggtccgga ctcctacggg aggcagcagt ggggaatatt ggacaatggg  360
ggcaaccctg atccagccat gccgcgtgtg tgaagaaggc cttttggttg taaagcactt  420
taagcaggga ggagaggcta atggttaata cccattagat tagacgttac ctgcagaata  480
agcaccggct aactctgtgc cagcagccgc ggtaatacag agggtgcgag cgttaatcgg  540
aattactggg cgtaaagcga gtgtaggtgg ctcattaagt cacatgtgaa atccccgggc  600
ttaacctggg aactgcatgt gatactggtg gtgctagaat atgtgagagg gaagtagaat  660
tccaggtgta gcggtgaaat gcgtagagat ctggaggaat accgatggcg aaggcagctt  720
cctggcataa tattgacact gagattcgaa agcgtgggta gcaaacagga ttagataccc  780
tggtagtcca cgccgtaaac gatgtctact agccgttggg gtccttgaga ctttagtggc  840
gcagttaacg cgataagtag accgcctggg gagtacggcc gcaaggttaa aactcaaatg  900
aattgacggg ggcccgcaca gcggtggagc atgtggttt aattcgatgc aacgcgaaga  960
accttacctg gtcttgacat agtgagaatc ytkcagagat gmgggagtgc cttcgggaat 1020
tcacatacag gtgctgcatg gctgtcgtca gctcgtgtcg tgagatgttg ggttaagtcc 1080
cgcaacgagc gcaaccctt tccttatttg ccagcgggtt aagccgggaa ctttaaggat 1140
actgccagtg acaaactgga ggaaggcggg gacgacgtca gtcatcatg gcccttacga 1200 ccagggctac acacgtgcta caatggtagg tacagagggt tgctacacag cgatgtgatg 1260
ctaatctcaa aaagcctatc gtagtccgga ttggagtctg caactcgact ccatgaagtc 1320
ggaatcgcta gtaatcgcag atcagaatgc tgcggtgaat acgttcccgg gccttgtaca 1380
caccgcccgt cacaccatgg gagtctattg caccagaagt aggtagccta acgcaagagg 1440
gcgcttacca cggtgtggtc gatgactggg gtgaagtcgt aacaaggtag cc         1492

<210> SEQ ID NO 3
<211> LENGTH: 1483
<212> TYPE: DNA
<213> ORGANISM: Moraxella osloensis ATCC19976 strain

<400> SEQUENCE: 3
gagtttgatc ctggctcaga ttgaacgctg gcggcaggct taacacatgc aagtcgaacg   60
atgactctct agcttgctag agatgattag tggcggacgg gtgagtaaca tttaggaatc  120
tacctagtag tgggggatag ctcggggaaa ctcgaattaa taccgcatac gacctacggg  180
tgaaaggggg cgcaagctct tgctattaga tgagcctaaa tcagattagc tagttggtgg  240
ggtaaaggcc caccaaggcg acgatctgta actggtctga gaggatgatc agtcacaccg  300
gaactgagac acggtccgga ctcctacggg aggcagcagt ggggaatatt ggacaatggg  360
```

-continued

```
ggcaaccctg atccagccat gccgcgtgtg tgaagaaggc cttttggttg taaagcactt      420
taagcaggga ggagaggcta atggttaata cccattagat tagacgttac ctgcagaata      480
agcaccggct aactctgtgc cagcagccgc ggtaatacag agggtgcgag cgttaatcgg      540
aattactggg cgtaaagcga gtgtaggtgg ctcattaagt cacatgtgaa atccccgggc      600
ttaacctggg aactgcatgt gatactggtg gtgctagaat atgtgagagg gaagtagaat      660
tccaggtgta gcggtgaaat gcgtagagat ctggaggaat accgatggcg aaggcagctt      720
cctggcataa tattgacact gagattcgaa agcgtgggta gcaaacagga ttagataccc      780
tggtagtcca cgccgtaaac gatgtctact agccgttggg gtccttgaga ctttagtggc      840
gcagttaacg cgataagtag accgcctggg gagtacggcc gcaaggttaa aactcaaatg      900
aattgacggg ggcccgcaca agcggtggag catgtggttt aattcgatgc aacgcgaaga      960
accttacctg gtcttgacat agtgagaatc tytcagagat gagagagtgc cttcgggaac     1020
tcacatacag gtgctgcatg gctgtcgtca gctcgtgtcg tgagatgttg ggttaagtcc     1080
cgcaacgagc gcaacccttt tccttatttg ccagcgggtt aagccgggaa ctttaaggat     1140
actgccagtg acaaactgga ggaaggcggg gacgacgtca agtcatcatg gcccttacga     1200
ccagggctac acacgtgcta caatggtagg tacagagggt tgctacacag cgatgtgatg     1260
ctaatctcaa aaagcctatc gtagtccgga ttggagtctg caactcgact ccatgaagtc     1320
ggaatcgcta gtaatcgcgg atcagaatgc cgcggtgaat acgttccgg gccttgtaca      1380 caccgcccgt cacaccatgg gagtctattg caccagaagt aggtagccta acgaaagagg     1440
gcgcttacca cggtgtggtc gatgactggg gtgaagtcgt aac                       1483
```

METHOD OF SCREENING FOR A DAMP-DRY MALODOR INHIBITOR AND METHOD OF EVALUATING DAMP-DRY MALODOR INHIBITOR BY MICROBIAL PRODUCTION OF 4-METHYL-3-HEXENOIC ACID

This application is a National Stage application filed under Rule 371 based on PCT/JP2011/069950 filed Sep. 1, 2011, which claims priority to Japan 2011-083031filed Apr. 4, 2011 which claims priority to Japan 2010-211459 filed Sep. 21, 2010.

TECHNICAL FIELD

The present invention relates to a method of screening a damp-dry malodor inhibitor and a method of evaluating a damp-dry malodor inhibitor.

BACKGROUND ART

Fabric products, for example, sanitary products such as towels and bedclothes, and garments (hereinafter, in the present specification, also simply referred to as "fabric products") provide a comfortable sense of use and wear sensation when the products are kept clean. Furthermore, fabric products such as sanitary products and garments are materials that are put on human bodies, and towels, bedclothes and the like are used by being brought into direct contact with human bodies. Therefore, it is important even from the viewpoint of hygiene to keep these materials clean. Along the enhanced recent social requirements for hygiene, the public interest in keeping fabric products such as sanitary products and garments clean has increased.

In recent years, as consumers build up more interest in the living environment, it is desired more than ever to remove any unpleasant odors (in the present specification, also referred to as "foul malodor") of personal belongings. The odors that cling to fabric products, for example, sanitary products such as towels and bedclothes, and garments, include external factors such as cigarettes, as well as internal factors that re originated from human body, which are produced by repeated use of fabric products.

Fabric products that are brought into direct contact with human skin, including underclothes, towels, handkerchiefs and the like, or fabric products that have a potential to absorb or attach sweat containing sebum, corneous substances and the like, may produce a wet-and-dirty dustcloth-malodor-like characteristic malodor in a case where after laundry, laundered fabric products are left untouched in a damp place such as the inside of a laundering machine tub for a long time, in the case of having been dried indoors, in the case of having gotten wet with rain or sweat, or in the case of insufficiently dried fabric products. This malodor is generally called a damp-dry malodor, and this odor can be mostly eliminated by sufficiently drying the fabric products. However, even for fabric products which have been sufficiently dried and from which no damp-dry malodor is sensed, when the fabric products become damp due to sweat, rain or the like, the damp-dry malodor may be produced. If fabric products once produce this damp-dry malodor, the damp-dry malodor can be temporarily eliminated by sufficiently drying the fabric products after laundry, but the wet-and-dirty dustcloth-like damp-dry malodor is likely to recur at the time of use. Such a damp-dry malodor that is prone to recur may be produced not only in a case where fabric products are dried indoors, but also in a case where a dryer or a washing machine having a low temperature drying function is used, and even in the case of fabric products that have been dried outdoors, if the fabric products become damp.

A feature of the recurrent damp-dry malodor lies in that the malodor is not produced, or mostly reduced, if a fabric product has been laundered and sufficiently dried. However, the fabric product produces the malodor only by becoming damp. The recurrent damp-dry malodor is likely to be produced when fabric products are stored in a wardrobe or the like for a long time. However, fabric products such as underclothes, handkerchiefs or towels, which are frequently brought into contact with human skin and are used with a high use frequency and a short period of the wash-use cycle, are in many cases such that once this damp-dry malodor is produced, the malodor comes to recur during use.

Furthermore, as the number of times of laundering increases, the intensity of malodor of the damp-dry malodor tends to increase. In order to inhibit this damp-dry malodor, it is important to treat fabric products so as not to produce such damp-dry malodor-causing substances. As a method for that purpose, there is a demand for an agent which inhibits the damp-dry malodor. Also, there is a demand for the development of a method of screening a damp-dry malodor inhibitor and a method of evaluating a damp-dry malodor inhibitor.

It has been hitherto reported that the damp-dry malodor is a complex odor composed of the "mold-like malodor" of medium-chain aldehydes, medium-chain alcohols, ketones and the like, the "sour malodor" of short-chain fatty acids, medium-chain fatty acids and the like, the "fishy malodor" of nitrogen compounds, and sulfur compounds, and medium-chain fatty acids in particular have a high degree of contribution (see Non-Patent Literature 1). Furthermore, Non-Patent Literature 1 describes that a major component of the damp-dry malodor is speculated to be "a mixture of unsaturated fatty acids having a branched structure with 7 to 9 carbon atoms," and these are also contained in the foul odor of human sweat or the like. As indicator substances for the damp-dry malodor, various kinds of fatty acids including 4-methyl-3-hexenoic acid have been hitherto suggested (see Patent Literature 1). The 4-methyl-3-hexenoic acid is naturally known as a component of citrons (see Non-Patent Literature 2), and it is also known that the 4-methyl-3-hexenoic acid is produced from terpenes by microorganisms (see Patent Literature 2). However, these literatures do not describe or suggest the mechanism of the production of the damp-dry malodor. Also, these literatures do not disclose the relation between various kinds of fatty acids including the 4-methyl-3-hexenoic acid and the recurrence of the damp-dry malodor. Furthermore, there is no instance of devising a method of screening a damp-dry malodor inhibitor and a method of evaluating a damp-dry malodor inhibitor based on such a mechanism.

PRIOR ART LITERATURE

Patent Literatures

Patent Literature 1: JP-A-2009-244094("JP-A" means unexamined published Japanese patent application)
Patent Literature 2: JP-A-56-124387

Non-Patent Literatures

Non-Patent Literature 1: Hanihara, Sonoda, "The Detergent Curbing Malodor in Indoor Laundry Drying," Fragrances, September 2004, No. 223, p. 109-116

Non-Patent Literature 2: Proceedings of the 53$^{rd}$ Forum on Fragrances/Terpenes, and Oil Refinery Chemistry (2009), p. 4-6

SUMMARY OF INVENTION

Technical Problem

The present invention resides in to provide a method of screening a damp-dry malodor inhibitor, by which a damp-dry malodor inhibitor can be screened conveniently with high accuracy. Further, the present invention resides in to provide a method of evaluating a damp-dry malodor inhibitor, by which the damp-dry malodor inhibitory function can be evaluated conveniently with high accuracy.

Solution to Problem

In view of the points described above, the inventors of the present invention conducted a thorough investigation from the viewpoints of the causative substances, causative bacteria, and the mechanism of occurrence of the damp-dry malodor. As a result, regarding the causative substances of the damp-dry malodor, although medium-chain branched fatty acids such as 4-methyl-3-hexanoic acid, 4-methyl-3-hexenoic acid, 5-methyl-2-hexanoic acid, and 5-methyl-2-hexenoic acid have already been known, it was found that among these, 4-methyl-3-hexenoic acid in particular has a particularly low threshold value as compared with other substances, and is a main causative substance. Furthermore, it was found that among the damp-dry malodors, a recurrent damp-dry malodor that relapses as a fabric product sufficiently dries and then becomes damp, is a malodor that is produced when, even after the damp-dry malodor has been sufficiently eliminated after drying, particular microorganisms survive in the fabric product or proliferate therein, and thereby produce damp-dry malodor-causing substances from a sebaceous dirt component remaining in the fabric product, or that the malodor that has been caught by the fabric as a result of drying is liberated again by wetting of the fabric product, and is easily perceived due to a low threshold. It was also found that the relevant damp-dry malodor is greatly affected by 4-methyl-3-hexenoic acid, and it was found that the production of such a damp-dry malodor involves microorganisms having a 4-methyl-3-hexenoic acid production capacity. Microorganisms that produce 4-methyl-3-hexenoic acid from terpenes are conventionally known. However, it is not yet fully known that microorganisms produce a damp-dry malodor-causing substance, or 4-methyl-3-hexenoic acid, in the presence of a sebaceous dirt component, and the inventors of the present invention have newly found this.

The present invention was accomplished based on these findings.

The present invention relates to a method of screening a damp-dry malodor inhibitor, containing the steps of: bringing microorganisms having a 4-methyl-3-hexenoic acid production capacity into contact with a test substance in the presence of a sebaceous dirt component; detecting the production of a damp-dry malodor-causing substance by the microorganisms; and thereby selecting a test substance having a damp-dry malodor inhibitory function.

Further, the present invention relates to a method of evaluating a damp-dry malodor inhibitor, containing the steps of: bringing microorganisms having a 4-methyl-3-hexenoic acid production capacity into contact with a test substance in the presence of a sebaceous dirt component; detecting the production of a damp-dry malodor-causing substance by the microorganisms; and thereby evaluating the damp-dry malodor inhibitory function of the test substance.

Further, the present invention relates to a kit for screening of a damp-dry malodor inhibitor containing a sebaceous dirt component and microorganisms having a 4-methyl-3-hexenoic acid production capacity.

Further, the present invention relates to a kit for evaluation of a damp-dry malodor inhibitor containing a sebaceous dirt component and microorganisms having a 4-methyl-3-hexenoic acid production capacity.

Advantageous Effects of Invention

According to the method of screening a damp-dry malodor inhibitor of the present invention, a damp-dry malodor inhibitor can be screened conveniently with high accuracy. Furthermore, according to the method of evaluating a damp-dry malodor inhibitor of the present invention, the damp-dry malodor inhibitory function of a damp-dry malodor inhibitor can be evaluated conveniently with high accuracy.

Other and further features and advantages of the invention will appear more fully from the following description.

MODE FOR CARRYING OUT THE INVENTION

The method of screening a damp-dry malodor inhibitor of the present invention contains steps of bringing microorganisms having a 4-methyl-3-hexenoic acid (in the present specification, also called 4M3H) production capacity into contact with a test substance in the presence of a sebaceous dirt component, detecting the production of a damp-dry malodor-causing substance by the microorganisms, and thereby selecting a test substance having a damp-dry malodor inhibitory function. According to the method of screening a damp-dry malodor inhibitor of the present invention, high accuracy screening of a damp-dry malodor inhibitor can be conveniently carried out.

Furthermore, the method of evaluating a damp-dry malodor inhibitor of the present invention contains steps of bringing microorganisms having a 4M3H production capacity into contact with a test substance in the presence of a sebaceous dirt component, detecting the production of a damp-dry malodor-causing substance by the microorganisms, and thereby evaluating the damp-dry malodor inhibitory function of the test substance. According to the method of evaluating a damp-dry malodor inhibitor of the present invention, for example, as for a substance that has been selected as a candidate for a damp-dry malodor inhibitor, a high accuracy evaluation of the damp-dry malodor inhibitory function of the substance can be conveniently carried out.

In the present specification, the term "damp-dry malodor" means a malodor that is generated from a fabric product in a case where the fabric product that has been used is laundered and insufficiently dried, or in a case where the fabric product becomes damp. However, there are occasions in which, although the damp-dry malodor may be temporarily eliminated by sufficiently drying a fabric product, a wet-and-dirty dustcloth-like damp-dry malodor recurs from a fabric product immediately after drying or as soon as the fabric product is reused after storage, or some while after starting of using the fabric product, or due to the moisture of rain, sweat or the like. As such, the wet-and-dirty dustcloth-like damp-dry malodor that recurs when a fabric product from which a damp-dry malodor has been temporarily eliminated by sufficient drying becomes damp, may be referred to as a "recurrent damp-dry malodor" or a "recurrent malodor" in the present specification.

The damp-dry malodor that is produced because of insufficient drying after laundering of a fabric product, is a complex odor of a S (sulfur) odor, a N (nitrogen) odor, an aldehyde odor, a lower fatty acid odor, and a medium-chain branched fatty acid odor including the 4M3H odor. The recurrent wet-and-dirty dustcloth-like unpleasant odor that recurs from a fabric product due to the moisture of rain, sweat or the like after the fabric product has been sufficiently dried to eliminate the damp-dry malodor, is mostly the medium-chain branched fatty acid odor which is mainly composed of the 4M3H odor, and other highly volatile malodor such as the S odor, the N odor and the aldehyde odor is hardly produced.

Furthermore, the term "inhabitation of damp-dry malodor" includes inhibition of a damp-dry malodor, and prevention of the production of a damp-dry malodor. In the present invention, the term is defined to characteristically refer to the inhibition of the recurrent damp-dry malodor, particularly the 4M3H odor, as the damp-dry malodor.

Meanwhile, "4-methyl-3-hexenoic acid" has cis- and trans-isomers as described below. In the present invention, the compound is intended to include compounds of both the cis-structure and the trans-structure.

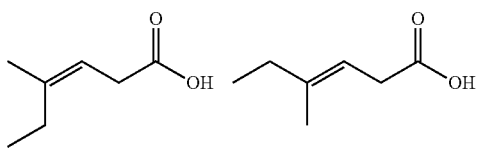

There are no particular limitations on the action mechanism of the "damp-dry malodor inhibitor" in the present invention. Examples of the action mechanism of the damp-dry malodor inhibitor includes sterilization of microorganisms that cling into a fabric product, prevention of the conversion of sweat, sebum or the like that remain in a fabric product to a damp-dry malodor-causing substance, decomposition or conversion of a damp-dry malodor-causing substance into an odorless substance, and masking of a damp-dry malodor. The action mechanism of the damp-dry malodor inhibitor in the present invention may be of any kind.

The "microorganisms having a 4M3H production capacity" in the present invention includes the microbial cells themselves of microorganisms having a 4M3H production capacity, as well as crushed cells, a microbial cell culture fluid, a crude extract originating from microorganisms having a 4M3H production capacity, and a processed product of microbial cells, such as a purified enzyme.

A method of obtaining microorganisms having a 4M3H production capacity that is used in the present invention will be described. There are no particular limitations on the method of obtaining microorganisms having a 4M3H production capacity, but examples thereof include: (1) a method of performing a sensory evaluation of fabric products, and consequently isolating a microbial strain from a fabric product that emits a damp-dry malodor; (2) a method of isolating microorganisms that exist in a fabric product, measuring the 4M3H production capacity of the isolated microorganisms, and selecting a microbial strain having a 4M3H production capacity (3) a method of measuring the 4M3H production capacity of microorganisms that have been isolated from the environment or acquired from a microorganism depository, and selecting a microbial strain having a 4M3H production capacity; and (4) a method of comparing the sequence similarity of a particular gene sequence with the gene sequence of a microbial strain having a 4M3H production capacity, and selecting a microbial strain having higher sequence similarity. Microorganisms having a 4M3H production capacity may be selected by any one method among the methods described above, or microorganisms having a 4M3H production capacity may be also selected by combining two or more of the methods.

The method of obtaining microorganisms having a 4M3H production capacity to be used in the present invention will be specifically described. However, the present invention is not intended to be limited to these.

First, the outline of the method (1) (a method of performing a sensory evaluation of fabric products, and isolating a microbial strain from a fabric product that emits a damp-dry malodor) will be explained.

At home or the like, fabric products that have been used after being laundered, or stored after being laundered (unused after being laundered), for example, towels, T-shirts, pillow covers, and underclothes are collected, and fabric products from which a strong damp-dry malodor can be perceived by a sensory evaluation are selected. The selected fabric products are cut out to a certain size (for example, 5×5 cm, 2×2 cm), and the fabric products are added to a lecithin polysorbate (also referred to as LP in the present specification) dilution (manufactured by Nihon Pharmaceutical Co., Ltd.), physiological saline or the like. Subsequently, an extract liquid obtained by stirring is plated on an agar medium such as a lecithin polysorbate-added soybean casein digest (also referred to as SCD-LP in the present specification) agar medium (manufactured by Nihon Pharmaceutical Co., Ltd.) or a potato dextrose agar (also referred to as PDA in the present specification) medium (manufactured by Becton Dickinson Co.), and cultured for a certain time (for example, 35° C., 24 hours), and then microorganisms are isolated from the colonies thus obtained.

The various microbial strains thus isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces, or the microbial strains are subjected to solid culture or liquid culture in the presence of a sebaceous dirt component. Subsequently, microbial strains producing damp-dry malodor are selected by a sensory evaluation. In the case where identification of the various microbial strains that have been selected is required, there are no limitations on the identification method. However, the identification can be carried out by determining a base sequence having a length of about 500 bp in the upstream region of 16S rDNA gene in a bacterium, and a base sequence having a length of about 200 to 500 bp in the D2 region of LSU (Large Subunit) in a fungus; and analyzing the sequence similarity of the base sequence with the corresponding base sequence of a reference strain. Meanwhile, the sequence similarity of base sequences may be also calculated by using a genetic information processing software, Clustal W (http://dustalw.ddbj.nig.ac.jp/top-j.htm), or the like.

Next, the outline of the method (2) (a method of isolating microorganisms that exist in a fabric product, measuring the 4M3H production capacity of the isolated microorganisms, and selecting a microbial strain having a 4M3H production capacity) will be explained.

At home or the like, fabric products that have been used after being laundered, or stored after being laundered (unused after being laundered), for example, towels, T-shirts, pillow covers and underclothes, are collected and cut out to a certain size (for example, 5×5 cm, 2×2 cm). The fabric products are added to a LP dilution (manufactured by Nihon Pharmaceutical Co., Ltd.), physiological saline or the like. Subsequently, an extract liquid obtained by stirring is plated on an agar medium such as a SCD-LP agar medium (manufactured by Nihon Pharmaceutical Co., Ltd.) or a PDA medium (manufactured by Becton Dickinson Co.), and cultured for a certain time (for example, 35° C., 24 hours), and then microorganisms are isolated from the colonies thus obtained.

The various microbial strains thus isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces, or the microbial strains are subjected to solid culture or liquid culture in the presence of a sebaceous dirt component. Subsequently, production of 4M3H is detected, and thereby microbial strains which are recognized to produce 4M3H are selected. In the case where identification of the various microbial strains that have been selected is required, there are no limitations on the identification method. However, for example, the identification can be carried out by determining a base sequence having a length of about 500 bp in the upstream region of 16S rDNA gene in a bacterium, and a base sequence having a length of about 200 to 500 bp in the D2 region of LSU in a fungus; and analyzing the sequence similarity of the base sequence with the corresponding base sequence of a reference strain. Meanwhile, the sequence similarity of base sequences may be also calculated by using a genetic information processing software, Clustal W, or the like.

Next, the method (3) (a method of measuring the 4M3H production capacity of microorganisms that have been isolated from the environment or acquired from a microorganism depository, and selecting a microbial strain having a 4M3H production capacity) will be explained.

Microbial strains are purchased from institutions for microorganism distribution such as ATCC (American Type Culture Collection), NBRC (NITE Biological Resource Center), JCM (Japan Collection of Microorganisms), and NCIMB (National Collection of Industrial Marine and Food Bacteria).

Alternatively, microbial strains are isolated using a SCD-LP agar medium (manufactured by Nihon Pharmaceutical Co., Ltd.), a PDA medium (manufactured by Becton Dickinson Co.) or the like by a routine method from various environments such as soils, plants, river water, and inside dwellings; and then microbial strains are isolated. Meanwhile, there are no particular limitations on the medium used herein.

The various microbial strains that have been purchased or isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces, or the microbial strains are subjected to solid culture or liquid culture in the presence of a sebaceous dirt component. Subsequently, production of 4M3H is detected, and thereby microbial strains which are recognized to produce 4M3H are selected. In the case where identification is required to the various microbial strains that have been selected from the microorganisms isolated from the environment, there are no limitations on the identification method. For example, identification can be carried out by determining a base sequence having a length of about 500 bp in the upstream region of 16S rDNA gene in a bacterium, and a base sequence having a length of about 200 to 500 bp in the D2 region of LSU in a fungus; and analyzing the sequence similarity of the base sequence with the corresponding base sequence of a reference strain. Meanwhile, the sequence similarity of base sequences may be also calculated by using a genetic information processing software, Clustal W, or the like.

Next, the outline of the method (4) (a method of comparing the sequence similarity of a particular gene sequence with the gene sequence of a microbial strain having a 4M3H production capacity, and selecting a microbial strain having higher sequence similarity) will be explained.

First, the base sequence of a particular gene of the microbial strain having a 4M3H production capacity that has been selected by the method (1), method (2), and/or method (3) as described above, is determined. Then, microorganisms having a base sequence having high sequence similarity with the base sequence thus determined are selected, and thereby a microbial strain having the 4M3H production capacity to be used in the present invention can be obtained. For example, as shown in Examples described below, since *Moraxella* sp. 4-1, *Moraxela* sp. 4-4, *Moraxella osloensis* ATCC19976, and the like are causative bacteria of damp-dry malodor, they can be selected as reference microbial strains having the 4M3H production capacity. Next, for example, as described in SEQ ID NOS:1, 2 and 3, the base sequence of the region of 16S rDNA or the like of the reference samples is determined. Then, a microbial strain having a base sequence having high sequence similarity with the entirety or a portion of the base sequence of the reference samples thus determined is selected. Here, the term "having high sequence similarity" implies that the sequence similarity with the base sequence of a reference sample, such as the base sequence set forth in any one of SEQ ID NOS:1 to 3, is preferably 95% or more, more preferably 97% or more, further preferably 98% or more, and particularly preferably 99% or more. Meanwhile, *Moraxella* sp. 4-1 was deposited with the International Patent Organism Depositary at the National Institute of Advanced Industrial Science and Technology (address: Central 6, 1-1, Higashi 1-chome, Tsukuba-shi. Ibaraki-ken) on Aug. 22, 2011, under the Accession No. FERM BP-11394.

The base sequence of microorganisms can be determined by an ordinary method. Furthermore, the sequence similarity of a base sequence is calculated by the Lipman-Pearson method (Science, 227, 1435, 1985) or the like. Specifically, the sequence similarity of a base sequence can be calculated by using a sequence similarity analysis (Search Homology) program of a genetic information processing software, Genetyx-Win (manufactured by Software Development, Inc.), and carrying out an analysis by taking the Unit size to compare (ktup) parameter as 2.

The microorganisms that are used in the present invention are not particulary limited as long as the microorganisms are microorganisms having a 4M3H production capacity, and are microorganisms which produce 4M3H in the presence of a sebaceous component. For example. the microorganisms are preferably at least one kind of microbial strain selected from the genus *Moraxelia, Acinetobacter, Pseudomonas, Bacillus, Sphinoomonas, Ralstonia, Curiavidus, Psychorobacter, Serratia, Escherichi Staphvococcus, Burkholderia, Saccaromyces* and *Rhodotrula*; more preferably at least one kind of microbial strain selected from the species of *Moraxella* sp., *Moraxella osloensis, Acinetobacter radioresistens, Aqinetobacter juni, Acinetobter calcoaceticus, Serratia marcescens, Escherichia coli, Stahylococcus aureus, Pseudomonas alcalaenes, Bacillus cereus, Bacillus subtilis, Pschrobactr pacificensis, Psychrobacter glacincola, Sphingomonas yanoikuyae, Ralstoni* sp., *Saccaromyces cerevisiae, Rhodotorula mucilaginoa, Rhodotorula slooffiae, Cupriavidus oxalaticus* and *Burkholderia cepacia*; further preferably at least one kind of microbial strain selected from the species of *Moraxella* sp., *Moraxella osloensis, Pseudomonas alcaliaenes, Raistonia* sp., *Saccaromvces cerevisiae, Rhodotogria mucilacinosa* and *Rhodotrula slooffiae*; and particularly preferably at least one kind of microbial strain selected from the species of *Moraxella* sp. and *Moraxella osloensis*.

In the present invention, regarding the microorganisms having a 4M3H production capacity, one kind of microorganism may be used, or two or more kinds of microorganisms may be also used in combination. Meanwhile, in the present invention, "*Moraxella* sp." means a microbial species having a base sequence in which the base sequence of 16S rDNA gene has a sequence similarity of 95% or more, more preferably 97% or more, further preferably 98% or more, and particularly preferably 99% or more, with the base sequence of SEQ ID NO:1, 2 or 3.

In the present specification, the term "sebaceous dirt" means the most representative dirt that clings to fabric products such as garments. The sebaceous dirt contains large amounts of oil components such as free fatty acids and glycerides, and those components trapping the carbon in dust, days, exfoliated comeous substances, and the like are observed as sebaceous dirt in fabric products and the like.

The sebaceous dirt component that is used in the present invention is not particularly limited as long as it is a component of sebaceous dirt that can be usually seen in garments and the like. However, a substance which has a potential to be a precursor of a damp-dry malodor-causing substance that is produced from fabric products, is preferred. Examples of the substance which has a potential to be a precursor of a damp-dry malodor-causing substance that is produced from fabric products, include anteiso fatty acids having 9 to 21 carbon atoms (preferably 11 to 19 carbon atoms, and more preferably 17 to 19 carbon atoms). Among these, compounds that are not actually present in the sebaceous dirt are also included. However, in the present specification, it is intended that these anteiso fatty acids are also included in the sebaceous dirt component. In the present invention, the sebaceous dirt component is preferably an anteiso fatty acid. The anteiso fatty acid that is preferably used in the present invention may be any of a saturated fatty acid and an unsaturated fatty acid, and it is defined that salts and esters of anteiso fatty acids are also included in the anteiso fatty acid. Specific examples thereof include 6-methyloctanoic acid, 8-methyldecanoic acid, 12-methyletradecanoic acid, 14-methylhexadecanoic acid, 16-methyloctadecanoic acid, 14-methylhexadecenoic acid, and 16-methyloctadecenoic acid, and salts, esters and the like of these acids.

The anteiso fatty acid that is preferably used in the present invention can be synthesized by an ordinary method (see, for example, JP-A-2009-149548). Furthermore, commercially available products can be also obtained from Sigma-Aldrich Company or the like and used.

In the method of screening a damp-dry malodor inhibitor and the method of evaluating a damp-dry malodor inhibitor of the present invention, the microorganisms having the 4M3H production capacity as described above are brought into contact with a test substance in the presence of a sebaceous dirt component, and the microorganisms are incubated together with the test substance and the sebaceous dirt component. There are no particular limitations on the conditions for incubation, but it is preferable to carry out the incubation under humidified conditions at 25° C. to 35° C. for 3 hours to 72 hours (preferably 8 to 72 hours). Furthermore, when microorganisms are brought into contact with a test substance, and/or when microorganisms are incubated, sterilized water or a buffer solution may be added to the microorganisms, or medium components such as sugars, peptones produced from casein, peptones produced from soybean, a yeast extract, inorganic salts, a pH adjusting agent, and agar may be also added to those sterilized water and buffer solution. Alternatively, a commercially available medium may be also used directly or after diluting. Also, when incubation is carried out in the liquid state, it is preferable to shake the medium, and when incubation is carried out in the solid state, it is preferable to leave the medium to stand still.

In the present invention, microorganisms having a 4M3H production capacity and a test substance that are used in the present invention may be added to a fabric product to which a sebaceous dirt component is clung for bringing the microorganisms and the test substance into contact with each other, and the microorganisms may be incubated together with the test substance and the sebaceous dirt component. In this case, there are no particular limitations on the conditions for incubation, but it is preferable to carry out the incubation by allowing the system to stand still at 25° C. to 35° C. for 3 hours to 48 hours (preferably 8 to 48 hours). Furthermore, the sebaceous dirt component may have clung to the fabric product from the beginning, or a sebaceous dirt component such as an anteiso fatty acid may be caused to cling to the fabric product. In the case of causing the sebaceous dirt component to cling to the fabric product, it is preferable to cause the sebaceous dirt component to cling to a fabric product having a size of 2×2 cm at a proportion of 0.1 mg to 1 mg.

There are no particular limitations on the amount of addition of the microorganisms to a fabric product, but a microorganism suspension is preferably added to a fabric product to obtain a microbial population of $10^2$ CFU/cm$^2$ to $10^5$ CFU/cm$^2$.

There are no particular limitations on the material of the fabric product that can be used in the present invention, and the material may be any of natural materials such as wool, silk and cotton; chemical fabrics such as polyester and polyamide; and combinations thereof. In the present invention, the material of the fabric product is preferably cotton. Furthermore, in the case of using a fabric product after adding a sebaceous dirt component thereto, the fabric product may be an unused product, or may be a used product that has been used once or more. In the case of using a fabric product without adding a sebaceous dirt component thereto, a fabric product that has been used once or more is used as received, or is used after being laundered.

In the present invention, the microorganisms and the test substance may be brought into contact with each other in a solid or solution containing a sebaceous dirt component. Specifically, a test substance may be added in advance into an agar medium containing a sebaceous dirt component or applied in advance on the medium, microorganisms having a 4M3H production capacity may be plated thereon, and the microorganisms and a sebaceous dirt component may be brought into contact with each other in the presence of the test substance. Alternatively, a liquid medium containing a sebaceous dirt component and a test substance may be mixed, microorganisms having a 4M3H production capacity are inoculated thereto, and the microorganisms and the sebaceous dirt component may be brought into contact with each other in the presence of the test substance. The medium used herein may be appropriately selected in accordance with the microorganism species having a 4M3H production capacity.

In the present invention, there are no particular limitations on the contact ratio (mixing ratio) of the microorganisms having a 4M3H production capacity and the sebaceous dirt component, but 0.1 mg to 10 mg of the sebaceous dirt component such as an anteiso fatty acid may be preferably brought into contact with the microorganisms at a final concentration of $10^1$ CFU to $10^8$ CFU.

In the screening method and the evaluation method of the present invention, a test substance having a damp-dry malodor inhibitory function is selected by detecting the production of a damp-dry malodor-causing substance by the microorganisms.

The damp-dry malodor-causing substance may be any substance that is produced by the microorganisms having a 4M3H production capacity and has a potential to become a damp-dry malodor-causing substance. Examples thereof include 4-methyl-3-hexenoic acid (4M3H), 4-methyl-3-pentenoic acid, and 4-methyl-3-octenoic acid. In the present invention, it is preferable to detect the production of 4M3H.

In the screening method and the evaluation method of the present invention, there are no particular limitations on the method of detecting the production of a damp-dry malodor-causing substance. And the detection may be carried out according to a qualitative method such as a sensory evaluation, or the production of a damp-dry malodor-causing substance may be also quantitatively detected by using column chromatography or the like. Furthermore, as shown in JP-A-2009-244094, a chromophore may be introduced into a carboxyl group of a damp-dry malodor-causing substance, and the presence or absence of the damp-dry malodor-causing substance, or the amount of the damp-dry malodor-causing substance present may be determined by utilizing a color reaction.

Specifically, a calibration curve of a damp-dry malodor-causing substance is produced in advance, and an instrumental analysis may be carried out by using this calibration curve. Alternatively, an altered substance or an unaltered substance of the damp-dry malodor-causing substance may be quantitatively determined by a chemical analysis based on titration, extraction or the like. Furthermore, the damp-dry malodor-causing substance may be also examined on the basis of the difference in the intensity of malodor resulting from the presence or absence of the addition of a damp-dry malodor inhibitor, or on the basis of the change in the type of malodor, by a sensory evaluation.

In the screening method of the present invention, the production of a damp-dry malodor-causing substance by microorganisms having a 4M3H production capacity can be detected, and a test substance having a damp-dry malodor inhibitory function can be selected as a damp-dry malodor inhibitor. Furthermore, in the method of evaluating a damp-dry malodor inhibitor, the production of a damp-dry malodor-causing substance by microorganisms having a 4M3H production capacity can be detected, and the damp-dry malodor inhibitory function of a test substance can be evaluated.

Regarding the test substance that is used in the screening method and the evaluation method of the present invention, any substance may be used, and the test substance may be any of a low molecular weight compound and a high molecular weight compound, the kind of the test substance not being particularly limited. Specific examples of the test substance include, for example, inorganic salts, surfactants, proteins, antibodies, peptides, polypeptides, oligonucleotides, polynucleotides, DNAs, RNAs, lipids, sugars, polysaccharides, natural extracts, fragrances, and combinations thereof.

A kit for screening of a damp-dry malodor inhibitor and a kit for evaluation of a damp-dry malodor inhibitor of the present invention each contain a sebaceous dirt component and microorganisms having a 4-methyl-3-hexenoic acid production capacity. In the kits of the present invention, there are no particular limitations on the specific constitution examples other than the sebaceous dirt component and the microorganisms having a 4-methyl-3-hexenoic acid production capacity, but for example, objects such as the following may be employed.

(1) An anteiso fatty acid as the sebaceous dirt component
(2) An apparatus that detects the damp-dry malodor-causing substance such as 4M3H
(3) A fabric product to which the sebaceous dirt component is caused to cling (for example, a cotton fabric product that has been used)
(4) A solution or a solid, which is brought into contact with the microorganisms and the test substance (for example, physiological saline, a buffer solution, a liquid medium, or a solid medium)

EXAMPLES

The present invention will be described in more detail based on examples given below, but the invention is not meant to be limited by these.

Test Example 1

Identification of Damp-Dry Malodor-causing substance

Cotton towels which produced strong damp-dry malodor after laundering and drying were collected from homes, and 50 g of each towel was cut out. The malodor components were extracted therefrom with 500 mL of dichloromethane, and then the extract was concentrated under reduced pressure. Furthermore, 200 mL of a 1M aqueous solution of sodium hydroxide was added to the extract solution, an aqueous layer was collected, and 200 mL of 2M hydrochloric acid was added to the aqueous layer to make it acidic. To this solution, 200 mL of dichloromethane was added, the organic layer was concentrated under reduced pressure, and a concentrate of acidic components was adjusted to a constant volume of 1 mL.

Subsequently, the concentrate was fractionated by using a gas chromatography apparatus manufactured by Agilent Technologies, Inc. connected with Preparative Fraction Collector (PFC) apparatus manufactured by Gerstel GmbH & Co. KG, on the basis of the GC retention time under the following conditions, and the GC30 fraction in the vicinity of the intended component was captured into 200 mg of a filler (trade name: TENAX TA, manufactured by GL Sciences, Inc.) that was filled in a glass tube having an internal diameter of 6 mm and a length of 117 mm.

(GC-PFC Conditions)

GC: Agilent 6890N (trade name, manufactured by Agilent Technologies, Inc.)

Column: DB-1 (trade name, manufactured by Agilent Technologies, Inc.), length: m, internal diameter: 0.53 mm, film thickness: 1 μm 40° C. 1 min. hold→6° C./min. to 60° C.→4° C./min. to 300° C.

Injection volume: 2 μL

PFC: Trap time 18 min. to 24 min., 30 times

Trap: TENAX TA (trade name, manufactured by GL Sciences, Inc.) 200 mg

Finally, the intended component captured in TENAX was analyzed with an apparatus in which Thermal Desorption System (TDS) manufactured by Gerstel GmbH & Co. KG connected to GC-MS manufactured by Agilent Technologies, Inc., under the following conditions.
(TDS-GC-MS Conditions)
GC: Agilent 6890N (trade name, manufactured by Agilent Technologies, Inc.)
MS: Agilent 5973 (trade name, manufactured by Agilent Technologies, Inc.)
TDS desorption conditions: 250° C., purge flow rate: 50 mL/min, purge time: 3 min.
Column: DB-FFAP (trade name, manufactured by Agilent Technologies, Inc.), length: 30 m, internal diameter: 250 µm, film thickness: 0.25 µm 40° C. 1 min. hold→6° C./min. to 60° C.→2° C./min. to 240° C.

As a result of the analysis, it was made clear that the damp-dry malodor-causing substance is medium-chain branched fatty acids including 4M3H.

(2) Test for Damp-Dry Malodor Reproduction in Fabric Products

The various microbial strains that had been isolated as described above were respectively inoculated into sterilized samples of cotton towels that had produced a damp-dry malodor or cotton towels that had been laundered after use and stored, and the microbial strains were cultured under humidified conditions (humidity: 100%) at 35° C. for 24 hours. Subsequently, the presence or absence of the production of a damp-dry malodor was determined by expert evaluators (N=3) who had been trained for a fragrance evaluation, by agreement, on the basis of the following criteria.
1: A very strong damp-dry malodor was produced.
2: A strong damp-dry malodor was produced.
3: A weak damp-dry malodor was produced.
4: No damp-dry malodor was produced.

The results are shown in Table 1.

TABLE 1

| Kind of microbial strain | Towel 1 | Towel 2 | Towel 3 | Bath towel 1 | Bath towel 2 | Bath towel 3 | Bath towel 4 | Bath towel 5 | Production of damp-dry malodor |
|---|---|---|---|---|---|---|---|---|---|
| *Micrococcus* sp. | ○ | ○ | ○ | ○ | ○ | ○ | ○ | ○ | 4 |
| *Escherichia hermannii* | — | — | — | ○ | — | — | ○ | — | 4 |
| *Pseudomanas* sp. | ○ | — | ○ | ○ | ○ | ○ | — | — | 4 |
| *Moraxella* sp. | ○ | ○ | ○ | ○ | ○ | ○ | ○ | ○ | 1 |
| *Roseomonas* sp. | ○ | — | ○ | ○ | — | — | ○ | — | 4 |
| *Bacillus cereus* | — | — | — | ○ | — | — | ○ | — | 3 |
| Others | ○ | ○ | — | — | — | — | — | — | 4 |

○: Microbial strain was isolated.
—: Microbial strain was not isolated.

Test Example 2

Identification of Damp-Dry Malodor-causing bacteria (1) Isolation of Microbial Strains A solution in 0.1 mL obtained by cutting out a cotton towel or bath towel which produced a damp-dry malodor after laundering and drying, adding a LP dilution (manufactured by Nihon Pharmaceutical Co., Ltd.) thereto, and then stirring the mixture was plated on a SCD-LP agar medium (manufactured by Nihon Pharmaceutical Co., Ltd.) and cultured at 35° C. for 24 hours. The microorganisms were isolated from the colonies thus obtained. Identification of the isolated bacterial strains was carried out by determining a base sequence having a length of about 500 bp in the upstream region of 16S rDNA gene, and identification of the isolated yeast strains was carried out by determining a base sequence having a length of about 200 to 500 bp in the D2 region of LSU, based on the sequence similarity of the relevant base sequences with reference strains. The sequence similarity of a base sequence was calculated by using a genetic information processing software, Clustal W. Furthermore, in connection with *Moraxella* sp., the base sequence of *Moraxella osloensis* ATCC19976 was determined, and identification was achieved by comparing a subject base sequence with the reference base sequence.

The microbial strains isolated from various towels or bath towels are shown in Table 1.

According to the results of Table 1, *Moraxella* sp. was isolated from all the towels and bath towels that produced a damp-dry malodor. Also, there was a large number of isolated *Moraxella* sp. Furthermore, it was confirmed that when the isolated *Moraxella* sp. was inoculated into sterilized towels that had produced a damp-dry malodor, a very strong damp-dry malodor was produced.

Therefore, it was made clear that damp-dry malodor involves particular microorganisms such as the subject microbial species.

Test Example 3

Selection of Microorganisms Having 4M3H Production Capacity

The 4M3H production capacity of microbial strains that had been isolated and identified according to Test Example 2 described above; microbial strains that had been isolated from the environment (soil and inside dwellings) by a standard method by using a soybean casein digest (also called SCD in the present specification) agar medium or a PDA medium, and then had been isolated and identified; and microorganisms that had been obtained from microorganism depositories, was measured.

Meanwhile, the microbial strains obtained from microorganism depositories are as follows.
*Moraxella osloensis* NCIMB10693 (purchased from NCIMB (National collection of industrial and marine bacteria))
*Moraxella osoensis* ATCC19976 (purchased from ATCC (American Type Culture Collection))

*Psychrobacter immobilis* NBRC15733, *Psychrobacter pacificensis* NBRC103191,
*Psychrobacter glacincola* NBRC101053, *Pseudomonas aeruginosa* NBRC13275,
*Pseudomonas putida* NBRC14164, *Sphingomonas yanoikuyae* NBRC15102,
*Micrococcus luteus* NBRC3333, *Brevundimonas diminuta* NBRC12697,
*Roseomonas aerilata* NBRC106435, *Cupriavidus oxalaticus* NBRC13593,
*Pseudoxanthomonas* sp. NBRC101033, *Serratia marcescens* NBRC12648.
*Enterobacter cloacae* NBRC3320, *Corynebacterium efficiens* NBRC100395,
*Escherichia coli* NBRC3972, *Staphylococcus aureus* NBRC13276,
*Saccaromyces cerevisiae* NBRC1661, *Candida albicans* NBRC1061, *Alcaligenes faecalis* NBRC13111, *Burkholderia cepacia* NBRC15124 and *Rhodotorula mucilaginosa* NBRC0909 (each purchased from NBRC (NITE Biological Resource Center))
*Bacillus cereus* JCM2152, *Bacillus subtilis* JCM1465 and *Lactobacillus plantarum* JCM1149 (purchased from JCM (Japan Collection of Microorganisms))

Furthermore, in regard to the *Moraxella* bacteria, the sequence similarity of the base sequence in the 16S rDNA gene region of each bacterium with the base sequence set forth in SEQ ID NO:1, SEQ ID NO:2 or SEQ ID NO:3 was determined. Meanwhile, the base sequences set forth in SEQ ID NO:1, SEQ ID NO:2 and SEQ ID NO:3 represent the base sequences of the 16S rDNA gene regions of *Moraxella* sp. 4-1, *Moraxella* sp. 4-4 and *Moraxella osloensis* ATCC19976, respectively. Furthermore, the sequence similarity of the base sequences was calculated by using a genetic information processing software, Clustal W. Meanwhile, *Moraxella* sp. 4-1 was deposited with the International Patent Organism Depositary at the National Institute of Advanced Industrial Science and Technology (address: Central 6, 1-1, Higashi 1-chome, Tsukuba-shi, Ibaraki-ken) on Aug. 22, 2011, under the Accession No. FERM BP-11394.

The results are shown in Table 2.

TABLE 2

| Sample No. | Strain Name | | Sequence similarity with the base sequence set forth in SEQ ID NO:1 | | Sequence similarity with the base sequence set forth in SEQ ID NO:2 | | Sequence similarity with the base sequence set forth in SEQ ID NO:3 | |
|---|---|---|---|---|---|---|---|---|
| | | | Upstream 504 bp | 1484 bp | Upstream 504 bp | 1484 bp | Upstream 504 bp | 1484 bp |
| 1 | *Moraxella osloensis* | NCIMB 10693 | 99.2 | 99.2 | 100 | 99.7 | 100 | 99.9 |
| 2 | *Moraxella osloensis* | ATCC19976 | 99.2 | 99.3 | 100 | 99.7 | 100 | 100 |
| 3 | *Moraxella* sp. (isolated strain) | No. 12 | — | — | — | — | — | — |
| 4 | *Moraxella* sp. (isolated strain) | No. 37 | — | — | — | — | — | — |
| 5 | *Moraxella* sp. (isolated strain) | N1-52 | 100 | — | 99.6 | — | 99.6 | — |
| 6 | *Moraxella* sp. (isolated strain) | N1-37 | 100 | — | 99.2 | — | 99.2 | — |
| 7 | *Moraxella* sp. (isolated strain) | O1-35 | — | — | — | — | — | — |
| 8 | *Moraxella* sp. (isolated strain) | 4-1 | 100 | 100 | 99.2 | 99.7 | 99.2 | 99.3 |
| 9 | *Moraxella* sp. (isolated strain) | 4-3 | 100 | — | 99.2 | — | 99.2 | — |
| 10 | *Moraxella* sp. (isolated strain) | 4-4 | 99.2 | 99.7 | 100 | 100 | 100 | 99.7 |
| 11 | *Moraxella* sp. (isolated strain) | 4-5 | 100 | — | 99.4 | — | 99.4 | — |
| 12 | *Moraxella* sp. (isolated strain) | 4-6 | 100 | — | 99.8 | — | 99.8 | — |
| 13 | *Moraxella* sp. (isolated strain) | 4-7 | 99.8 | — | 99.2 | — | 99.2 | — |
| 14 | *Moraxella* sp. (isolated strain) | 4-8 | 100 | — | 99.2 | — | 99.2 | — |
| 15 | *Moraxella* sp. (isolated strain) | 4-9 | 99.8 | — | 99.8 | — | 99.8 | — |

TABLE 2

| Sample No. | Strain Name | | Sequence similarity with the base sequence set forth in SEQ ID NO:1 | | Sequence similarity with the base sequence set forth in SEQ ID NO:2 | | Sequence similarity with the base sequence set forth in SEQ ID NO:3 | |
|---|---|---|---|---|---|---|---|---|
| | | | Upstream 504 bp | 1484 bp | Upstream 504 bp | 1484 bp | Upstream 504 bp | 1484 bp |
| 16 | *Moraxella* sp. (isolated strain) | 4-10 | 100 | — | 99.4 | — | 99.4 | — |
| 17 | *Moraxella* sp. (isolated strain) | 4-11 | 100 | — | 99.4 | — | 99.4 | — |
| 18 | *Moraxella* sp. (isolated strain) | 4-12 | 100 | — | 99.2 | — | 99.2 | — |
| 19 | *Moraxella* sp. (isolated strain) | N1-52 | 100 | — | 99.6 | — | 99.6 | — |
| 20 | *Moraxella* sp. (isolated strain) | N1-37 | 100 | — | 99.2 | — | 99.2 | — |
| 21 | *Micrococcus* sp. (isolated strain) | 6755-01 | 72.6 | — | 72.2 | — | 72.2 | — |
| 22 | *Roseomonas* sp. (isolated strain) | 7546-04 | 71.2 | — | 71.0 | — | 71.0 | — |
| 23 | *Bacillus cereus* | 7546-05 | 68.9 | — | 68.5 | — | 68.5 | — |
| 24 | *Pseudomonas* sp. (isolated strain) | 7546-03 | 83.5 | — | 83.1 | — | 83.1 | — |
| 25 | *Acinetobacter* sp. (isolated strain) | 7546-06 | 83.3 | — | 83.1 | — | 83.1 | — |
| 26 | *Escherichia coli* | 7546-01 | 79.4 | — | 79.2 | — | 79.2 | — |
| 27 | Sterile distilled water | | — | — | — | — | — | — |

1. Selection Using Fabric Products that Had been Used

One platinum loop of each of the microbial strains thus obtained was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 1.0.

Towel samples were prepared by cutting a used cotton towel that had been repeatedly used and laundered in a domestic environment, into squares each having a size of 5 cm×5 cm and sterilizing the cut pieces, and 0.1 mL each of the various microbial suspensions were inoculated into the towel samples. The inoculated samples were left to stand still under humidified conditions at 37° C. for 24 hours.

The presence or absence of a damp-dry malodor in the used cotton towel obtained after standing still for 24 hours was determined by expert evaluators (N=3) by agreement. In regard to the evaluation criteria, a sample from which a strong damp-dry malodor was perceived was rated as "⊙"; a sample from which a damp-dry malodor was perceived was rated as "○"; a sample from which a slight damp-dry malodor was perceived was rated as "Δ"; and a sample from which no damp-dry malodor was perceived was rated as "x". The results are shown in Table 3.

TABLE 3

| | | | Sensory evaluation results | |
|---|---|---|---|---|
| No. | Strain | | Used towel 1 | Used towel 2 |
| 3-1 | Moraxella osloensis | NCIMB10693 | ⊙ | ⊙ |
| 3-2 | Moraxella osloensis | ATCC19976 | ⊙ | ⊙ |
| 3-3 | Moraxella sp. | 4-1 (isolated strain) | ⊙ | ⊙ |
| 3-4 | Sphingomonas yanoikuyae | No. 18 (isolated strain) | ○ | ○ |
| 3-5 | Acinetobacter junii | 7546-06 (isolated strain) | ○ | ○ |
| 3-6 | Micrococcus luteus | 105-14 (isolated strain) | x | x |
| 3-7 | Pseudoxanthomonas sp. | 101-17 (isolated strain) | x | x |

2. Selection Using Fabric Products Having a Sebaceous Dirt Component Applied Thereon 14-Methylhexadecanoic acid was synthesized by a two-step reaction such as described below, according to JP-A-2009-149546.

Step (a)

11.9 g (60.0 mmol) of 12-dodecanolide and 24.3 g (96.0 mmol, 1.6 equivalents) of a 32% (hydrogen bromide)/(acetic acid) solution were introduced into a 100-mL autoclave protected with Teflon (registered trademark), and the autoclave was purged with nitrogen and then sealed. The content in the autoclave was stirred with a magnetic stirrer for 16 hours by using an oil bath at 60° C. After cooling the mixture, 14 mL of water was added thereto, and the mixture was transferred into a separatory funnel by using 200 mL of hot hexane. The mixture was washed with ion-exchanged water, dried over magnesium sulfate, filtered, and crystallized from n-hexane. Thus, 14.4 g (yield: 86%) of 12-bromododecanoic acid was obtained.

Step (b)

Subsequently, in a 100-mL four-necked flask equipped with a refluxing cooling tube, a 50-mL separatory funnel, a magnetic stirrer, and a temperature sensor, 5.0 g (17.9 mmol) of 12-bromododecanoic acid and 28.2 mg (0.006 eq) of triphenylphosphine (manufactured by Kanto Chemical Co., Inc.) were introduced, and the mixture was dried under reduced pressure. In an argon atmosphere, 77.1 mg (0.03 equivalents) of copper(I) bromide (manufactured by Sigma-Aldrich Co.) and 10 mL of anhydrous tetrahydrofuran were added thereto. 39.5 mL (3 equivalents, 1.36N tetrahydrofuran solution) of 2-methylbutylmagnesium bromide was added dropwise thereto over one hour at room temperature. The mixture was stirred for one hour, and then 50 mL of a 1N aqueous solution of hydrochloric acid was added to the mixture, and the mixture was extracted two times with 100 mL of hexane. The extract was washed two times with 50 mL of ion-exchanged water, and then was dried over magnesium sulfate. The resultant was filtered and concentrated under reduced pressure, and 3.9 g of a crude product was obtained.

The crude product was quantitatively determined by gas chromatography (column: manufactured by Agilent Technologies, Inc., trade name: Ultra-2, 30 m×0.2 mm×0.33 μm, DET300° C., INJ300° C., column temperature: 100° C.→300° C., 10° C./min) using octadecane as an internal standard. As a result, the yield was found to be 79%.

In this manner, 14-methylhexadecanoic acid was obtained from 12-dodecanolide at a total yield of 68%. The purity was 98%.

16-Methyloctadecanoic acid was synthesized by the same operation, except that in the step (a) of the synthesis process for 14-methylhexadecanoic acid described above, 12-dodecanolide was changed to 15-pentadodecanolide, and in the step (b), 2-methylbutylmagnesium bromide was changed to sec-butylmagnesium bromide. Thus, 16-methyloctadecanoic add was obtained from 15-pentadodecanolide at a total yield of 84%. The purity was 95%.

One platinum loop of each of various microbial strains was inoculated into mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 1.0.

On a plain-woven cotton fabric which had been cut to a square having a size of 2 cm×2 cm, a solution prepared by dissolving 0.5 mg of 14-methylhexadecanoic acid or 16-methyloctadecanoic acid that had been synthesized in the above in 0.1 mL of methanol was applied, and thereafter, methanol was dried to solid.

0.1 mL each of the various microbial suspensions described above was inoculated into the plain-woven cotton fabric described above, and the samples were left to stand still under humidified conditions at 37° C. for 24 hours. Thus, quantification of 4M3H and a sensory evaluation of a damp-dry malodor were carried out in the following manner.

(1) Quantification of 4M3H 10 mL of methanol was added to the towel that had been left to stand still for 24 hours, and 1 mL of the methanol was mixed with 1 mL of ADAM (9-anthrydiazomethanene, manufactured by Funakoshi Corp., 0.1 w/v %). The mixture was left to stand for 60 minutes at room temperature, and thus derivatization was carried out.

Thereafter, 10 µL of the solution was analyzed by using LC-FL (liquid chromatography apparatus: HITACHI ELITE LaChrom (trade name, manufactured by Hitachi, Ltd.), column: Lichrosphere 100 RP-8(e) (trade name, manufactured by Agilent Technologies, Inc., 5 µm×125 mm×4 mmφ), column temperature: 40° C., eluent a mixed solution of acetonitrile/water=7/3 (volume ratio), flow rate: 1.0 mL/min, detector: excitation wavelength (365 nm), measurement wavelength (412 nm)), and thereby quantification of 4M3H thus produced was carried out. In regard to the amount of production of 4M3H, a sample which produced 4M3H in an amount of more than 1 µg was rated as "⌊"; a sample which produced 4M3H in an amount of more than 0.1 µg and 1 µg or less was rated as "○"; a sample which produced 4M3H in an amount of more than 0 µg and 0.1 µg or less was rated as "Δ"; and a sample in which no 4M3H was detected was rated as "x". The results obtained when 14-methylhexadecanoic acid was applied are presented in Table 4, and the results obtained when 16-methyloctadecanoic acid was applied are presented in Table 5.

(2) Sensory Evaluation of Damp-dry malodor

The presence or absence of a damp-dry malodor in the plain-woven cotton fabric obtained after standing still for 24 hours was determined by expert evaluators (N=3). In regard to the evaluation criteria, a sample from which a strong damp-dry malodor was perceived was rated as "⌊"; a sample from which a damp-dry malodor was perceived was rated as "○"; a sample from which a slight damp-dry malodor was perceived was rated as "Δ"; and a sample from which no damp-dry malodor was perceived was rated as "x". The results obtained when 14-methylhexadecanoic acid was applied are presented in Table 4, and the results obtained when 16-methyloctadecanoic acid was applied are presented in Table 5.

TABLE 4

| No. | Strain | | Production amount of 4M3H | Sensory evaluation |
|---|---|---|---|---|
| 4-1 | *Moraxella osloensis* | NCIMB10693 | ⊙ | ⊙ |
| 4-2 | *Moraxella osloensis* | ATCC19976 | ⊙ | ○ |
| 4-3 | *Moraxella* sp. | No. 12 (isolated strain) | ⊙ | ⊙ |
| 4-4 | *Moraxella* sp. | No. 37 (isolated strain) | ⊙ | ⊙ |
| 4-5 | *Moraxella* sp. | N1-52 (isolated strain) | ⊙ | ⊙ |
| 4-6 | *Moraxella* sp. | N1-37 (isolated strain) | ⊙ | ⊙ |
| 4-7 | *Moraxella* sp. | O1-35 (isolated strain) | ⊙ | ⊙ |
| 4-8 | *Moraxella* sp. | 4-1 (isolated strain) | ⊙ | ⊙ |
| 4-9 | *Moraxella* sp. | 4-3 (isolated strain) | ⊙ | ⊙ |
| 4-10 | *Moraxella* sp. | 4-4 (isolated strain) | ⊙ | ⊙ |
| 4-11 | *Moraxella* sp. | 4-5 (isolated strain) | ⊙ | ⊙ |
| 4-12 | *Moraxella* sp. | 4-6 (isolated strain) | ⊙ | ⊙ |
| 4-13 | *Moraxella* sp. | 4-7 (isolated strain) | ⊙ | ○ |
| 4-14 | *Moraxella* sp. | 4-8 (isolated strain) | ⊙ | ⊙ |
| 4-15 | *Moraxella* sp. | 4-9 (isolated strain) | ⊙ | ⊙ |
| 4-16 | *Moraxella* sp. | 4-10 (isolated strain) | ⊙ | ⊙ |
| 4-17 | *Moraxella* sp. | 4-11 (isolated strain) | ⊙ | ⊙ |
| 4-18 | *Moraxella* sp. | 4-12 (isolated strain) | ⊙ | ⊙ |
| 4-19 | *Psychrobacter immobilis* | NBRC15733 | x | x |
| 4-20 | *Psychrobacter pacificensis* | NBRC103191 | ⊙ | ○ |
| 4-21 | *Psychrobacter glacincola* | NBRC101053 | Δ | Δ |
| 4-22 | *Pseudomonas alcaligenes* | No. 41 (isolated strain) | ⊙ | ⊙ |
| 4-23 | *Pseudomonas aeruginosa* | NBRC13275 | x | x |
| 4-24 | *Pseudomonas putida* | NBRC14164 | x | x |
| 4-25 | *Sphingomonas yanoikuyae* | No. 18 (isolated strain) | ○ | ○ |
| 4-26 | *Sphingomonas yanoikuyae* | NBRC15102 | ○ | ○ |
| 4-27 | *Acinetobacter junii* | HH2 3h-12 (isolated strain) | ○ | Δ |
| 4-28 | *Acinetobacter junii* | 7546-06 (isolated strain) | ○ | Δ |
| 4-29 | *Acinetobacter calcoaceticus* | HH2BD-49 (isolated strain) | ○ | ○ |
| 4-30 | *Acinetobacter radioresistens* | N1-60 (isolated strain) | ○ | Δ |
| 4-31 | *Micrococcus luteus* | 105-14 (isolated strain) | x | x |
| 4-32 | *Micrococcus luteus* | NBRC3333 | x | x |
| 4-33 | *Brevundimonas* sp. | HAMI-42 (isolated strain) | x | x |
| 4-34 | *Brevundomonas diminuta* | NBRC12697 | x | x |
| 4-35 | *Roseomonas* sp. | 7546-04 (isolated strain) | x | x |
| 4-36 | *Roseomonas aerilata* | NBRC106435 | x | x |
| 4-37 | *Xanthomonas* sp. | IM-10 (isolated strain) | x | x |
| 4-38 | *Ralstonia* sp. | IM-33 (isolated strain) | ⊙ | ⊙ |
| 4-39 | *Cupriavidus* sp. | FUMI-22 (isolated strain) | ○ | Δ |
| 4-40 | *Cupriavidus oxalaticus* | NBRC13593 | x | x |
| 4-41 | *Sphingobium* sp. | 7-18 (isolated strain) | x | x |
| 4-42 | *Pseudoxanthomonas* sp. | 101-17 (isolated strain) | Δ | x |
| 4-43 | *Pseudoxanthomonas* sp. | NBRC101033 | x | x |
| 4-44 | *Bacillus cereus* | 7546-05 (isolated strain) | ○ | ○ |
| 4-45 | *Bacillus cereus* | JCM2152 | ○ | ○ |
| 4-46 | *Bacillus subtilis* | JCM1465 | ○ | Δ |
| 4-47 | *Serratia marcescens* | NBRC12648 | ○ | Δ |

TABLE 4-continued

| No. | Strain | | Production amount of 4M3H | Sensory evaluation |
|---|---|---|---|---|
| 4-48 | Enterobacter cloacae | NBRC3320 | x | x |
| 4-49 | Corynebacterium efficiens | NBRC100395 | x | x |
| 4-50 | Escherichia coli | NBRC3972 | ○ | Δ |
| 4-51 | Staphylococcus aureus | NBRC13276 | ○ | Δ |
| 4-52 | Staphylococcus epidemidis | KUMI-2 (isolated strain) | x | x |
| 4-53 | Saccaromyces cerevisiae | NBRC1661 | ⊙ | ⊙ |
| 4-54 | Candida albicans | NBRC1061 | x | x |
| 4-55 | Lactobacillus plantarum | JCM1149 | x | x |
| 4-56 | Alcaligenes faecalis | NBRC13111 | x | x |
| 4-57 | Burkholderia cepacia | NBRC15124 | ○ | ○ |
| 4-58 | Rhodotorula mucilaginosa | NBRC0909 | ⊙ | ⊙ |
| 4-59 | Rhodotorula slooffiae | 13c (isolated strain) | ⊙ | ⊙ |

TABLE 5

| No. | Strain | | Production amount of 4M3H | Sensory evaluation |
|---|---|---|---|---|
| 5-1 | Moraxella osloensis | NCIMB10693 | ⊙ | ⊙ |
| 5-2 | Moraxella osloensis | ATCC19976 | ⊙ | ○ |
| 5-3 | Moraxella sp. | 4-1 (isolated strain) | ⊙ | ⊙ |

From the results of Tables 3, 4 and 5, it was understood that among various microorganisms, particular microorganisms such as genus *Moraxella. Acinetobacter, Pseudomonas, Bacillus, Sphingomonas, Cupriavidus, Ralstonia, Psychorobacter, Serratia, Eschericia, Staphylococcus, Burkholderia, Saccaromvces* and *Rhodotorula* have a 4M3H production capacity. Furthermore, it was made clear that such microorganisms having a 4M3H production capacity are involved in the production of a damp-dry malodor.

Furthermore, as for the microorganisms having a 4M3H production capacity that are used in the present invention, as described above, a sensory evaluation of fabric products may be carried out, and as a result, those microorganisms may be isolated from the fabric products which emit a damp-dry malodor. Alternatively, microorganisms existing in fabric products may be isolated, the 4M3H production capacity of the isolated microorganisms may be measured, and those microorganisms having a 4M3H production capacity may be selected. Furthermore, as can be seen from Tables 2 to 5, since there are microorganisms having very high sequence similarity of particular gene sequences among the microorganisms having a 4M3H production capacity, microorganisms having a 4M3H production capacity may be also selected by comparing the sequence similarity of particular gene sequences.

Example 1

One platinum loop of each of *Moraxella osloensis* NCIMB10693, *Moraxella* sp. 4-1, *Psychrobacter pacificensis* NBRC103191, *Psychrobacter glacincola* NCIMB101053, *Pseudomonas alcaligenes* No. 41, *Acinetobacter calcoaceticus* HH2BD-49, *Saccaromyces cerevisiae* NBRC1661, *Rhodotorula mucilaginosa* NBRC0909 and *Rhodotorula slooffiae* 13c was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 0.1.

On a plain-woven cotton fabric which had been cut to a square having a size of 2 cm×2 cm and sterilized under pressure, a solution prepared by dissolving 0.1 mg of 14-methylhexadecanoic acid that had been synthesized in Test Example 3 in 0.1 mL of methanol was applied, and thereafter, methanol was dried to solid.

Furthermore, 0.1 mL each of 10-ppm or 100-ppm aqueous solutions of the compounds shown in the following Table 6 was applied on the fabric described above. As a control, a fabric on which sterilized water was applied instead of the compounds described below was also prepared.

TABLE 6

| No. | Compound name |
|---|---|
| 6-1 | Alkyl benzyl dimethyl ammonium chloride (trade name: SANISOL C, manufactured by Kao Corporation) |
| 6-2 | Dodecyl trimethyl ammonium chloride (manufactured by Wako Pure Chemical Industries, Ltd.) |
| 6-3 | Tetradecyl trimethyl ammonium chloride (manufactured by Wako Pure Chemical Industries, Ltd.) |
| 6-4 | Hexadecyl trimethyl ammonium chloride (manufactured by Wako Pure Chemical Industries, Ltd.) |
| 6-5 | Palmitic acid (manufactured by Wako Pure Chemical Industries, Ltd.) |
| 6-6 | Stearic acid (manufactured by Wako Pure Chemical Industries, Ltd.) |
| 6-7 | Oleic acid (manufactured by KANTO CHEMICAL CO., INC.) |
| 6-8 | Linoleic acid (manufactured by KANTO CHEMICAL CO., INC.) |
| 6-9 | Linolenic acid (manufactured by KANTO CHEMICAL CO., INC.) |
| 6-10 | Polyoxyethylene (10) lauryl ether (trade name: EMULGEN 110, manufactured by Kao Corporation) |
| 6-11 | Sodium alkylbenzene sulfonate (trade name: NEOPELEX G65, manufactured by Kao Corporation) |
| 6-12 | Polylysine (manufactured by KANTO CHEMICAL CO., INC.) |
| 6-13 | Bis(4-dimethylaminodithiobenzil)nickel (trade name: Proxel BDN, manufactured by SUNWA CHEMICAL CO., LTD.) |
| 6-14 | Thymol (manufactured by KANTO CHEMICAL CO., INC.) |
| 6-15 | Cinnamic aldehyde (manufactured by KANTO CHEMICAL CO., INC.) |
| 6-16 | Dextrose (manufactured by Wako Pure Chemical Industries, Ltd.) |
| 6-17 | Peptone (manufactured by BD) |
| 6-18 | Sterile water |

On a plain-woven cotton fabric prepared as described above, 0.1 mL each of the various microbial suspensions was inoculated, and the samples were left to stand still under humidified conditions at 37° C. for 24 hours and were subjected to an evaluation such as described below.

(1) Quantification of 4M3H

Quantification of 4M3H was carried out by the same method as that used in Test Example 3, and by taking as a reference the 4M3H production amount of a sample on which sterilized water was applied as a test substance, the 4M3H production amounts in the case of applying other test substances were evaluated on the basis of the following criteria.

A: (4M3H production amount in the case of applying a test substance)<(1/100 of the 4M3H production amount in the case of applying sterilized water)

B: (1/100 of the 4M3H production amount in the case of applying sterilized water)≤(4M3H production amount in the case of applying a test substance)<(1/10 of the 4M3H production amount in the case of applying sterilized water)

C: (1/10 of the 4M3H production amount in the case of applying sterilized water)≤(4M3H production amount in the case of applying a test substance)<(4M3H production amount in the case of applying sterilized water)

D: (4M3H production amount in the case of applying sterilized water)≤(4M3H production amount in the case of applying a test substance)

The results are shown in Tables 7-1 and 7-2.

(2) Sensory Evaluation

A sensory evaluation of the damp-dry malodor was carried out by expert evaluators (N=3) by agreement on the basis of the following criteria.

A: The damp-dry malodor was suppressed, and the damp-dry malodor was hardly perceived.
B: The damp-dry malodor was almost inhibited.
C: The damp-dry malodor was slightly inhibited.
D: The damp-dry malodor was hardly inhibited, and a strong damp-dry malodor was perceived.

The results are shown in Tables 7-1 and 7-2.

TABLE 7-1

| Used strain | Substance to be tested | Conc./ppm | Production amount of 4M3H | Sensory evaluation |
|---|---|---|---|---|
| *M. osloensis* NCIMB10693 | Alkyl benzyl dimethyl ammonium chloride | 100 | D | D |
| | Dodecyl trimethyl ammonium chloride | 100 | C | D |
| | Tetradecyl trimethyl ammonium chloride | 100 | C | D |
| | Hexadecyl trimethyl ammonium chloride | 100 | D | D |
| | Palmitic acid | 100 | C | D |
| | Stearic acid | 100 | C | D |
| | Oleic acid | 100 | B | B |
| | Linoleic acid | 100 | B | B |
| | Linolenic acid | 100 | B | B |
| | Polyoxyethylene (10) lauryl ether | 100 | D | D |
| | Sodium akylbenzene sulfonate | 100 | C | D |
| | Polylysine | 10 | D | D |
| | | 100 | C | D |
| | Bis(4-dimethylaminodithiobenzil)nickel | 10 | C | C |
| | | 100 | A | A |
| | Thymol | 10 | B | B |
| | | 100 | A | B |
| | Cinnamic aldehyde | 10 | C | C |
| | | 100 | A | A |
| | Dextrose | 100 | D | D |
| | Peptone | 100 | D | D |
| | Sterile water | — | D | D |
| *Moraxella* sp. 4-1 | Alkyl benzyl dimethyl ammonium chloride | 100 | D | D |
| | Oleic acid | 100 | B | B |
| | Bis(4-dimethylaminodithiobenzil)nickel | 10 | B | D |
| | | 100 | A | A |
| | Thymol | 10 | C | B |
| | | 100 | B | B |
| | Dextrose | 100 | D | D |
| | Peptone | 100 | D | D |
| | Sterile water | — | D | D |
| *P. pacificensis* NBRC103191 | Alkyl benzyl dimethyl ammonium chloride | 100 | D | D |
| | Oleic acid | 100 | C | C |
| | Bis(4-dimethylaminodithiobenzil)nickel | 10 | C | D |
| | | 100 | B | B |
| | Thymol | 10 | D | D |
| | | 100 | B | D |
| | Dextrose | 100 | D | D |
| | Peptone | 100 | D | D |
| | Sterile water | — | D | D |
| *P. glacincola* NBRC101053 | Alkyl benzyl dimethyl ammonium chloride | 100 | C | D |
| | Oleic acid | 100 | A | A |
| | Bis(4-dimethylaminodithiobenzil)nickel | 10 | A | A |
| | | 100 | A | A |
| | Thymol | 10 | C | A |
| | | 100 | B | A |
| | Dextrose | 100 | D | D |
| | Peptone | 100 | D | D |
| | Sterile water | — | D | D |

TABLE 7-2

| Used strain | Substance to be tested | Conc./ppm | Production amount of 4M3H | Sensory evaluation |
|---|---|---|---|---|
| P. alcaligenes No. 41 | Alkyl benzyl dimethyl ammonium chloride | 100 | D | D |
| | Oleic acid | 100 | C | C |
| | Bis(4-dimethylaminodithiobenzil)nickel | 10 | C | D |
| | | 100 | A | A |
| | Thymol | 10 | D | D |
| | | 100 | C | D |
| | Dextrose | 100 | D | D |
| | Peptone | 100 | D | D |
| | Sterile water | — | D | D |
| A. calcoaceticus HH2BD-49 | Alkyl benzyl dimethyl ammonium chloride | 100 | D | D |
| | Oleic acid | 100 | C | D |
| | Bis(4-dimethylaminodithiobenzil)nickel | 10 | B | D |
| | | 100 | A | A |
| | Thymol | 10 | D | D |
| | | 100 | C | D |
| | Dextrose | 100 | D | D |
| | Peptone | 100 | D | D |
| | Sterile water | — | D | D |
| S. cerevisiae NBRC1661 | Alkyl benzyl dimethyl ammonium chloride | 100 | C | C |
| | Oleic acid | 100 | B | C |
| | Bis(4-dimethylaminodithiobenzil)nickel | 10 | C | C |
| | | 100 | A | A |
| | Thymol | 10 | C | C |
| | | 100 | D | C |
| | Dextrose | 100 | D | D |
| | Peptone | 100 | D | D |
| | Sterile water | — | D | D |
| R. muculaginosa NBRC0909 | Alkyl benzyl dimethyl ammonium chloride | 100 | D | D |
| | Oleic acid | 100 | B | C |
| | Bis(4-dimethylaminodithiobenzil)nickel | 10 | B | B |
| | | 100 | A | A |
| | Thymol | 10 | D | D |
| | | 100 | A | B |
| | Dextrose | 100 | D | D |
| | Peptone | 100 | D | D |
| | Sterile water | — | D | D |
| R. slooffiae 13c | Alkyl benzyl dimethyl ammonium chloride | 100 | D | C |
| | Oleic acid | 100 | C | C |
| | Bis(4-dimethylaminodithiobenzil)nickel | 10 | C | C |
| | | 100 | A | A |
| | Thymol | 10 | D | A |
| | | 100 | C | A |
| | Dextrose | 100 | D | D |
| | Peptone | 100 | D | D |
| | Sterile water | — | D | D |

As shown in Tables 7-1 and 7-2, according to the present invention, a screening of a damp-dry malodor inhibitor and an evaluation of a damp-dry malodor inhibitor are enabled.

Example 2

One platinum loop of each of *Moraxella osloensis* NCIMB10693, *Moraxella* sp. 4-1, *Acinetobacter* calcoaceticus HH2BD-49 and *Pseudomonas alcaliaenes* No. 41 was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 0.1.

Cotton bath towels or towels which had been used after being laundered at various homes were respectively cut to a size of 2 cm×2 cm, and were sterilized under pressure.

Furthermore, 0.1 mL each of 10-ppm or 100-ppm aqueous solutions of the compounds described in the above Table 6 was applied on the bath towels or towels described above. As a control, a fabric on which sterilized water was applied instead of the compounds described below was also prepared.

0.1 mL each of the various microbial suspensions was inoculated into the bath towels or towels prepared as described above, and the samples were left to stand still under humidified conditions at 37° C. for 24 hours. Thus, a sensory evaluation of a damp-dry malodor was carried out by the same method and the same evaluation criteria as those used in Example 1. The results are shown in Table 8.

TABLE 8

| Used strain | Substance to be tested | Conc./ppm | Sensory evaluation |
|---|---|---|---|
| M. osloensis NCIMB10693 | Alkyl benzyl dimethyl ammonium chloride | 100 | B |
| | Polyoxyethylene (10) lauryl ether | 100 | D |
| | Bis(4-dimethylamino-dithiobenzil)nickel | 10 | B |
| | | 100 | B |
| | Thymol | 10 | B |
| | | 100 | A |

TABLE 8-continued

| Used strain | Substance to be tested | Conc./ppm | Sensory evaluation |
|---|---|---|---|
| | Dextrose | 100 | D |
| | Peptone | 100 | D |
| | Sterile water | — | D |
| Moraxella sp. 4-1 | Alkyl benzyl dimethyl ammonium chloride | 100 | B |
| | Polyoxyethylene (10) lauryl ether | 100 | D |
| | Bis(4-dimethylamino-dithiobenzil)nickel | 10 | B |
| | | 100 | B |
| | Thymol | 10 | B |
| | | 100 | A |
| | Dextrose | 100 | D |
| | Peptone | 100 | D |
| | Sterile water | — | D |
| A. calcoaceticus HH2BD-49 | Alkyl benzyl dimethyl ammonium chloride | 100 | D |
| | Polyoxyethylene (10) lauryl ether | 100 | D |
| | Bis(4-dimethylamino-dithiobenzil)nickel | 10 | D |
| | | 100 | D |
| | Thymol | 10 | D |
| | | 100 | A |
| | Dextrose | 100 | D |
| | Peptone | 100 | D |
| | Sterile water | — | D |
| P. alcaligenes No. 41 | Alkyl benzyl dimethyl ammonium chloride | 100 | A |
| | Polyoxyethylene (10) lauryl ether | 100 | A |
| | Bis(4-dimethylamino-dithiobenzil)nickel | 10 | A |
| | | 100 | A |
| | Thymol | 10 | A |
| | | 100 | A |
| | Dextrose | 100 | D |
| | Peptone | 100 | D |
| | Sterile water | — | D |

As shown in Table 8, in the screening method and the evaluation method for a damp-dry malodor inhibitor of the present invention, even if fabric products that have been used after being laundered are used as the fabric products, a screening of a damp-dry malodor inhibitor and an evaluation of a damp-dry malodor inhibitor are enabled.

Example 3

One platinum loop of each of *Moraxella osloensis* NCIMB10693 and *Pseudomonas alcaligenes* No. 41 was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 0.1.

Was added 0.1 mg of 14-methylhexadecanoic acid synthesized in Test Example 3 to 1 mL of a SCD liquid medium (manufactured by Nihon Pharmaceutical Co., Ltd.). Thereon, 0.1 mL each of 10-ppm or 100-ppm aqueous solutions of the compounds described in the above Table 6 was applied. As a control, a liquid medium to which sterilized water was added instead of the compounds described below was also prepared.

Was inoculated 0.1 mL of each of the various microbial suspensions into the liquid medium prepared as described above, and the samples were subjected to shaking culture at 37° C. for 24 hours. Thus, a sensory evaluation of a damp-dry malodor was carried out by the same method and the same evaluation criteria as those used in Example 1. The results are shown in Table 9.

TABLE 9

| Used strain | Substance to be tested | Conc./ppm | Sensory evaluation |
|---|---|---|---|
| M. osloensis NCIMB10693 | Alkyl benzyl dimethyl ammonium chloride | 100 | A |
| | Polyoxyethylene (10) lauryl ether | 100 | D |
| | Bis(4-dimethylaminodithiobenzil)nickel | 10 | A |
| | | 100 | A |
| | Thymol | 10 | B |
| | | 100 | A |
| | Dextrose | 100 | D |
| | Peptone | 100 | D |
| | Sterile water | — | D |
| P. alcaligenes No. 41 | Alkyl benzyl dimethyl ammonium chloride | 100 | A |
| | Polyoxyethylene (10) lauryl ether | 100 | D |
| | Bis(4-dimethylaminodithiobenzil)nickel | 10 | A |
| | | 100 | A |
| | Thymol | 10 | D |
| | | 100 | A |
| | Dextrose | 100 | D |
| | Peptone | 100 | D |
| | Sterile water | — | D |

As shown in Table 9, in the screening method and the evaluation method for a damp-dry malodor inhibitor of the present invention, a screening of a damp-dry malodor inhibitor and an evaluation of a damp-dry malodor inhibitor are enabled by bringing microorganisms having a 4M3H production capacity and a test substance into contact in a liquid medium in the presence of a sebaceous dirt component.

Example 4

One platinum loop of *Moraxella osloensis* NCIMB10693 was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 0.1.

A solution prepared by dissolving 0.1 mg of 14-methylhexadecanoic acid synthesized in Test Example 3, in 0.1 mL of methanol was applied on a SCD agar medium. Thereon, 0.1 mL each of 10-ppm or 100-ppm aqueous solutions of the compounds described in the above Table 6 was applied. As a control, a agar medium on which sterilized water was applied instead of the compounds described below was also prepared.

Was inoculated 0.1 mL of each of the various microbial suspensions into the agar medium prepared as described above, and the samples were subjected to culture at 37° C. for 24 hours. Thus, a sensory evaluation of a damp-dry malodor was carried out by the same method and the same evaluation criteria as those used in Example 1. The results are shown in Table 10.

TABLE 10

| Used strain | Substance to be tested | Conc./ ppm | Sensory evaluation |
|---|---|---|---|
| *M. osloensis* NCIMB10693 | Alkyl benzyl dimethyl ammonium chloride | 100 | B |
| | Oleic acid | 100 | B |
| | Polyoxyethylene (10) lauryl ether | 100 | D |
| | Bis(4-dimethylaminodi-thiobenzil)nickel | 10 | C |
| | | 100 | B |
| | Thymol | 10 | D |
| | | 100 | C |
| | Dextrose | 100 | D |
| | Peptone | 100 | D |
| | Sterile water | — | D |

As shown in Table 10, in the screening method and the evaluation method for a damp-dry malodor inhibitor of the present invention, a screening of a damp-dry malodor inhibitor and an evaluation of a damp-dry malodor inhibitor are enabled by bringing microorganisms having a 4M3H production capacity and a test substance into contact in an agar medium in the presence of a sebaceous dirt component.

Having described our invention as related to the present embodiments, it is our intention that the invention not be limited by any of the details of the description, unless otherwise specified, but rather be construed broadly within its spirit and scope as set out in the accompanying Claims.

This non-provisional application Claims priority under 35 U.S.C. §119 (a) on Patent Application No. 2010-211459 filed in Japan on Sep. 21, 2010, and Patent Application No. 2011-083031 filed in Japan on Apr. 4, 2011, each of which is entirely herein incorporated by reference.

What is claimed is:

1. A method of screening for a test substance that is a damp-dry malodor inhibitor, comprising the steps of:
bringing microorganisms that produce 4-methyl-3-hexenoic acid into contact with the test substance in the presence of a sebaceous dirt component;
detecting production of 4-methyl-3-hexenoic acid by the microorganisms; and selecting a test substance that decreases production of 4-methyl-3-hexenoic acid as a damp-dry malodor inhibitor.

2. The method of screening a damp-dry malodor inhibitor according to claim 1, wherein the sebaceous dirt component is an anteiso fatty acid.

3. A method of evaluating whether a test substance is a damp-dry malodor inhibitor, comprising the steps of:
bringing microorganisms that produce 4-methyl-3-hexenoic acid into contact with the test substance in the presence of a sebaceous dirt component;
detecting the production of 4-methyl-3-hexenoic acid by the microorganisms; and evaluating the test substance as a damp-dry malodor inhibitor if the test substance decreases production of 4-methyl-3-hexenoic acid.

4. The method of evaluating a damp-dry malodor inhibitor according to claim 3, wherein the sebaceous dirt component is an anteiso fatty acid.

5. The method of screening a damp-dry malodor inhibitor according to claim 1, wherein the microorganisms and the test substance are added to a fabric product that contains the sebaceous dirt component, to bring the microorganisms and the test substance into contact with each other.

6. The method of screening a damp-dry malodor inhibitor according to claim 5, wherein the fabric product is a cotton fabric product that has been used.

7. The method of screening a damp-dry malodor inhibitor according to claim 1, wherein the microorganisms and the test substance are brought into contact with each other in a solution or solid containing the sebaceous dirt component.

8. The method of screening a damp-dry malodor inhibitor according to claim 1, wherein the microorganisms comprise at least one microbial strain from a genus selected from the group consisting of *Moraxella, Acinetobacter, Pseudomonas, Bacillus, Sphingomonas, Cupriavidus, Ralstonia, Psychorobacter, Serratia, Escherichia, Staphylococcus, Burkholderia, Saccaromyces* and *Rhodotorula*.

9. The method of screening a damp-dry malodor inhibitor according to claim 8, wherein the microorganisms comprise at least one microbial strain from a species selected from the group consisting of *Moraxella* sp., *Moraxella osloensis, Acinetobacter radioresistens, Acinetobacter junii, Acinetobacter calcoaceticus, Serratia marcescens, Escherichia coli, Staphylococcus aureus, Pseudomonas alcaligenes, Bacillus cereus, Bacillus subtilis, Psychrobacter pacificensis, Psychrobacter glacincola, Sphingomonas yanoikuyae, Ralstonia* sp., *Saccaromyces cerevisiae, Rhodotorula mucilaginosa, Rhodotorula slooffiae, Cupriavidus oxalaticus* and *Burkholderia cepacia*.

10. The method of evaluating a damp-dry malodor inhibitor according to claim 3, wherein the microorganisms and the test substance are added to a fabric product that contains the sebaceous dirt component, to bring the microorganisms and the test substance into contact with each other.

11. The method of evaluating a damp-dry malodor inhibitor according to claim 10, wherein the fabric product is a cotton fabric product that has been used.

12. The method of evaluating a damp-dry malodor inhibitor according to claim 3, wherein the microorganisms and the test substance are brought into contact with each other in a solution or solid containing the sebaceous dirt component.

13. The method of evaluating a damp-dry malodor inhibitor according to claim 3, wherein the microorganisms comprise at least one microbial strain from a genus selected from the group consisting of *Moraxella, Acinetobacter, Pseudomonas, Bacillus, Sphingomonas, Cupriavidus, Ralstonia, Psychorobacter, Serratia, Escherichia, Staphylococcus, Burkholderia, Saccaromyces* and *Rhodotorula*.

14. The method of evaluating a damp-dry malodor inhibitor according to claim 13, wherein the microorganisms comprise at least one of microbial strain from a species selected from the group consisting of *Moraxella* sp., *Moraxella osloensis, Acinetobacter radioresistens, Acinetobacter junii, Acinetobacter calcoaceticus, Serratia marcescens, Escherichia coli, Staphylococcus aureus, Pseudomonas alcaligenes, Bacillus cereus, Bacillus subtilis, Psychrobacter pacificensis, Psychrobacter glacincola, Sphingomonas yanoikuyae, Ralstonia* sp., *Saccaromyces cerevisiae, Rhodotorula mucilaginosa, Rhodotorula slooffiae, Cupriavidus oxalaticus* and *Burkholderia cepacia*.

* * * * *